United States Patent
Liu

(10) Patent No.: US 11,253,471 B2
(45) Date of Patent: Feb. 22, 2022

(54) **RECTAL MUCOSAL ADMINISTRATION PREPARATION OF *PULSATILLA CHINENSIS* SAPONIN B4 AND PREPARATION METHOD THEREFOR**

(71) Applicant: Qi Liu, Beijing (CN)

(72) Inventor: Qi Liu, Beijing (CN)

( * ) Notice: Subject to any disclaimer, the term of this patent is extended or adjusted under 35 U.S.C. 154(b) by 0 days.

(21) Appl. No.: 16/960,460

(22) PCT Filed: Jan. 8, 2018

(86) PCT No.: PCT/CN2018/071716
§ 371 (c)(1),
(2) Date: Jul. 7, 2020

(87) PCT Pub. No.: WO2019/134159
PCT Pub. Date: Jul. 11, 2019

(65) Prior Publication Data
US 2020/0330374 A1 Oct. 22, 2020

(51) Int. Cl.
| | | |
|---|---|---|
| *A61K 9/02* | (2006.01) | |
| *A61K 47/14* | (2017.01) | |
| *A61K 9/06* | (2006.01) | |
| *A61K 47/32* | (2006.01) | |
| *A61P 13/12* | (2006.01) | |
| *A61K 9/00* | (2006.01) | |
| *A61K 31/704* | (2006.01) | |
| *A61K 47/10* | (2017.01) | |
| *A61K 47/18* | (2017.01) | |
| *A61K 47/38* | (2006.01) | |

(52) U.S. Cl.
CPC .............. *A61K 9/0031* (2013.01); *A61K 9/02* (2013.01); *A61K 9/06* (2013.01); *A61K 31/704* (2013.01); *A61K 47/10* (2013.01); *A61K 47/14* (2013.01); *A61K 47/18* (2013.01); *A61K 47/38* (2013.01)

(58) Field of Classification Search
CPC .... A61K 31/704; A61K 9/0031; A61K 47/10; A61K 47/14; A61K 47/18; A61K 47/32; A61K 47/38; A61K 9/02; A61K 9/06; A61P 13/12
See application file for complete search history.

(56) References Cited

FOREIGN PATENT DOCUMENTS

| | | |
|---|---|---|
| CN | 1903174 A | 1/2007 |
| CN | 1903351 A | 1/2007 |
| CN | 103446237 A | 12/2013 |
| CN | 105193705 A | 12/2015 |
| CN | 105213410 A | 1/2016 |
| CN | 105535004 A | 5/2016 |
| CN | 105854021 A | 8/2016 |
| CN | 108938654 A | 12/2018 |
| KR | 20160019772 A * | 2/2016 ............... A61K 8/63 |

OTHER PUBLICATIONS

English translation by Google of KR20160019772A published on Feb. 22, 2016; 8 pages. (Year: 2016).*
Walter and Eliza Hall Institute ([online] retrieved on Jul. 22, 2021 from: https://www.eurekalert.org/pub_releases/2012-05/waeh-adm052312.php; May 2012; 2 pages) (Year: 2012).*
Fawaz et al. (International Journal of Pharmaceutics 2004;280:151-162) (Year: 2004).*
Mimaki et al. (J. Nat. Prod. 2001;64:1226-1229). (Year: 2001).*
Google translation of CN103446237A; 2013:7 pages. (Year: 2013).*
Googel translation of CN105213410A; 2016:7 pages. (Year: 2016).*
Ma, Weina et al.; The Research Progress of Medicinal Gels; Practical Pharmacy and Clinical Remedies; vol. 17, No. 204-12-31, pp. 1624-1628.

* cited by examiner

*Primary Examiner* — Ernst V Arnold
(74) *Attorney, Agent, or Firm* — Novick, Kim & Lee, PLLC; Allen Xue

(57) ABSTRACT

A rectal mucosal administration preparation of *Pulsatilla chinensis* (Bge.) Regel saponin B4 contains *Pulsatilla chinensis* (Bge.) Regel saponin B4 and a pharmaceutically acceptable substrate. The drug preparation is a rectal gel or a rectal suppository. Compared with oral administration, the rectal mucosal administration preparation of *Pulsatilla chinensis* (Bge.) Regel saponin B4 has a lower effective dose, and has a better medicinal effect at the same dose.

10 Claims, No Drawings

RECTAL MUCOSAL ADMINISTRATION PREPARATION OF *PULSATILLA CHINENSIS* SAPONIN B4 AND PREPARATION METHOD THEREFOR

TECHNICAL FIELD

The present invention belongs to the field of medicine and pharmaceutical preparation, and in particular relates to a new rectal mucosal administration preparation of *Pulsatilla chinensis* saponin B4, and the preparative method thereof.

BACKGROUND ART

Traditional Chinese medicine (TCM) *Pulsatilla chinensis* is the dry roots of plant *Pulsatilla chinensis* (Bge.) Regel, belonging to *Pulsatilla* genus of Ranunculaceae family. *P. chinensis* is first recorded in Shennong's herbal classic, as a common TCM. It has the functions of clearing away heat and detoxifying, cooling blood and stopping dysentery, removing dampness and destroying parasites, etc. Thus, *P. chinensis* is used for treatment of heat toxin and blood dysentery, warm malaria, chills and fever, epistaxis and blood hemorrhoids. Through modern pharmacological research, it is found that *P. chinensis* has more activities, such as broad-spectrum antibacterial activity, anti-tumor, anti-inflammatory, enhancing the immune function and so on.

There are abundant triterpenoid saponins in *Pulsatilla chinensis*. *Pulsatilla chinensis* saponin B4 belongs to pentacyclic triterpenoid saponin of lupine type, and it has a structure of formula 1.

discloses the use of the compound as an EV71 virus inhibitor in the preparation of anti HFMD drugs.

*Pulsatilla chinensis* saponin B4 contains five glycosyl groups, and has good water solubility. If the compound is administered orally (such as by gavage in animal experiments), the effective dose is large, resulting in a narrow safety window. Therefore, the inventor has filed an invention patent application (Application No. CN201710551726.8) entitled "An injectable preparation of *Pulsatilla chinensis* saponin B4". However, the injection may have a potential of hemolysis, so it is of positive significance to research and develop a new non-oral preparation of *Pulsatilla chinensis* aponin B4.

Except for administration by injection, non-oral administration routes include those via oral mucosa, nasal mucosa, lung, skin, rectal mucosa, eye, etc. Among them, rectal mucosa is rich in blood supply, and drug absorption is fast, as well as there are fewer interferent factors than oral absorption, such as the drug is not affected by gastrointestinal pH value. If the drug directly enters the lower rectal vein and anal vein through the mucosa, the first pass effect of liver can be avoided. Up to now, there is no report on the preparation for rectal mucosal administration of *Pulsatilla chinensis* aponin B4.

CONTENT OF THE INVENTION

In order to overcome the disadvantages of the prior art, the invention provides a new rectal mucosal administration preparation of *Pulsatilla chinensis* aponin B4.

In order to realize above objective, the following technical scheme is used in the present invention:

1

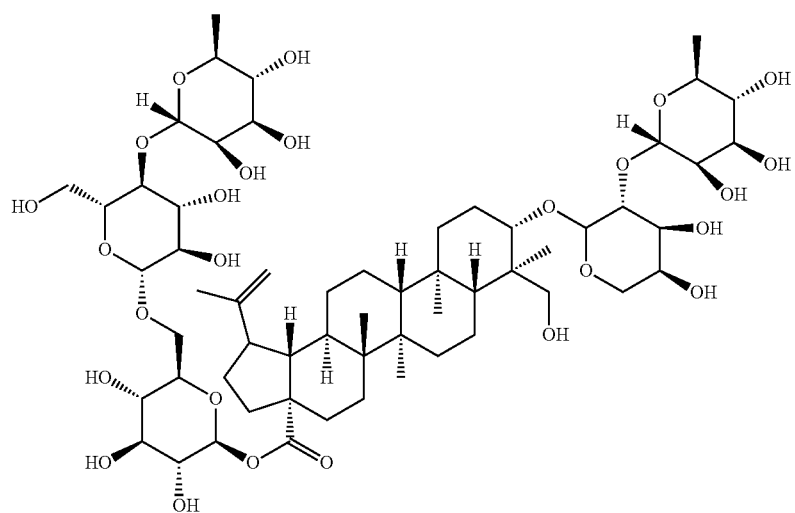

*Pulsatilla chinensis* saponin B4 has stronger activity. For example, the Chinese invention patent application number CN105213410 A (Publication date: Jan. 6, 2016) discloses the application of *Pulsatilla chinensis* saponin B4 as an immunomodulator in the drugs for treatment of acute inflammatory. Said acute inflammation includes acute renal injury, acute liver injury and acute lung injury caused by over-expression of inflammatory factors. For example, the Chinese invention patent application with the publication number of CN 105535004 A (publication date: May 4, 2016)

A rectal mucosal administration preparation of *Pulsatilla chinensis* saponin B4, comprising *Pulsatilla chinensis* saponin B4 and pharmaceutically acceptable substances;

Preferably, *Pulsatilla chinensis* saponin B4 is the only active component in the preparation delivered by rectal mucosa;

Preferably, said pharmaceutically acceptable substances are selected from one or more of acrylic resins, cellulose derivatives, ethylene polymers, natural gums, and fat suppository matrixs;

More preferably, said pharmaceutically acceptable substances are selected from one or more of carbomers, hydroxypropylmethylcelluloses, carboxymethylcellulose sodium and mixed fatty acid glycerides.

Preferably, the rectal mucosal administration preparation is selected from one or both of a rectal gel and a rectal suppository.

As a preferred embodiment, the present invention provides a rectal gel of *Pulsatilla chinensis* saponin B4, having a pH value of 6-7, and including effective amount of *Pulsatilla chinensis* saponin B4, as well as pharmaceutically acceptable substances selected from of one or more of carbomers, hydroxypropylmethylcelluloses, and sodium carboxymethylcelluloses, together with humectant, pH controlling agent and water.

The present invention further provides the method for preparation of rectal gel of *Pulsatilla chinensis* saponin B4, including the following procedures:

*Pulsatilla chinensis* saponin B4 is dissolved in water and filtered; said pharmaceutically acceptable substances and humectant are added under stirring to make the uniform dispersion; said pH controlling agent is added to adjust pH to 6-7, to provide the rectal gel;

Preferably, in said rectal gel of *Pulsatilla chinensis* saponin B4, said pharmaceutically acceptable base is carbomer, more preferably is one or both of carbomer 941 and carbomer 980; most preferably is carbomer 941;

Further preferably, based on the total mass of rectal gel of *Pulsatilla chinensis* saponin B4, the mass percent of carbomer 941 is 0.25%-1%, more preferably is 0.25%-0.5%, and most preferably is 0.4%-0.6%.

Preferably, in said rectal gel of *Pulsatilla chinensis* saponin B4, said humectant is selected from one or both of glycerol and propylene glycol, and more preferably, said humectant is glycerin;

Further preferably, based on the total mass of rectal gel of *Pulsatilla chinensis* saponin B4, the mass percent of glycerin is 5%-15%, and more preferably 5%-10%.

Preferably, said pH controlling agent is selected from one or more of triethanolamine, sodium hydroxide, ethylenediamine, laurylamine, and sodium bicarbonate; more preferably, said pH controlling agent is triethanolamine;

Further preferably, based on the total mass of rectal gel of *Pulsatilla chinensis* saponin B4, the mass percent of triethanolamine is 0.25%-1%, and more preferably 0.25%-0.5%.

As an especially preferable embodiment, the present invention provides a rectal gel of *Pulsatilla chinensis* saponin B4, having a pH value of 6-7, and including *Pulsatilla chinensis* saponin B4, carbomer 941, glycerol, triethanolamine, and water; based on the total mass of rectal gel of *Pulsatilla chinensis* saponin B4, the mass percentage of each ingredient is:

1%-20% for *Pulsatilla chinensis* saponin B4, 0.25%-0.5% for carbomer 941, 5%-10% for glycerol, 0.25%-5% for triethanolamine, and the remained percent for water;

Preferably, in above rectal gel of *Pulsatilla chinensis* saponin B4, the mass ratio of carbomer 941 to triethanolamine is 1:1.

Preferably, in above rectal gel of *Pulsatilla chinensis* saponin B4, the mass ratio of carbomer 941 to glycerol is 1:15-25, more preferably 1:20.

Preferably, in above rectal gel of *Pulsatilla chinensis* saponin B4, the mass ratio of carbomer 941 to water is 1:150-200, more preferably 1:180.

The present invention also provides the preparative method of said rectal gel of *Pulsatilla chinensis* saponin B4, including the following procedures:

According to the predetermined mass ratio, carbomer 941, glycerin, triethanolamine, and water are provided for use; according to the drug content of the rectal gel, *Pulsatilla chinensis* saponin B4 is prepared; *Pulsatilla chinensis* saponin B4 is dissolved in water and filtrated, to obtain the aqueous solution of *Pulsatilla chinensis* saponin B4; to the resultant solution is slowly added carbomer 941 under stirring, and the mixture is gently mixed; the mixture is further stirred, to which glycerin is added; triethanolamine is finally added to adjust pH to 6-7; stirring is continued until the swelling is uniform, and provided the rectal gel.

As another preferable embodiment, the present invention provides a rectal suppository of *Pulsatilla chinensis* saponin B4, including effective amount of *Pulsatilla chinensis* saponin B4 and the mixed fatty acid glycerides;

The present invention also provides the preparative method for the rectal suppository of *Pulsatilla chinensis* saponin B4, including the following procedures:

Said mixed fatty acid glycerides are taken out, heated till ⅔-¾ of them are melting, then stopped heating, and stirred till the matrix temperature is reduced to 50±2° C., to which is added *Pulsatilla chinensis* saponin B4. The mixture is stirred to disperse evenly, and injected into the suppository mould which has been evenly coated with liquid paraffin (the mould temperature being about 20° C.), and after cooling for 30 minutes, the overflow part is scraped off, then the rectal suppository is provided;

Preferably, the mixed fatty acid glyceride is selected from one or more of the mixed fatty acid glycerides 34, the mixed fatty acid glycerides 36, and the mixed fatty acid glycerides 38; more preferably, selected from one or both of the mixed fatty acid glycerides 34 or the mixed fatty acid glycerides 36; most preferably, selected from the mixed fatty acid glycerides 36.

The present invention also provides the preferable preparative method for the rectal suppository of *Pulsatilla chinensis* saponin B4, including the following procedures:

Said mixed fatty acid glycerides 36 are taken out, heated at the temperature of 55-60° C. till ⅔-¾ of them are melting, then stopped heating, and stirred till the matrix temperature is reduced to 50±2° C. to which is added *Pulsatilla chinensis* saponin B4. The mixture is stirred to disperse evenly, and injected into the suppository mould which has been evenly coated with liquid paraffin (the mould temperature being about 20° C.), and after cooling for 30 minutes, the overflow part is scraped off, then the rectal suppository is provided;

The present invention also provides the use of the rectal mucosal administration preparation of *Pulsatilla chinensis* saponin B4 in the preparation of drugs for treatment of acute renal injury.

The subject receiving the rectal mucosal administration preparation of *Pulsatilla chinensis* saponin B4 for treatment of acute renal injury is mammals, preferably humans.

The use according to the present invention includes that the effective dosage of the rectal mucosa administration preparation of *Pulsatilla chinensis* saponin B4 is placed in the subject in need thereof, preferably in human rectum at a distance of 2±1 cm from the anus.

When the rectal mucosal administration preparation of *Pulsatilla chinensis* saponin B4 according to the present invention is used for treatment of acute renal injury, the dosage is 8-32 mg/kg body weight, preferably 16-32 mg/kg body weight.

In this specification, unless otherwise indicated, said "*Pulsatilla chinensis* saponin B4" includes that (with a content ≥90% determined by HPLC) extracted, separated and purified from plants, as well as the composition mainly consisted of *Pulsatilla chinensis* saponin B4 (the content of *Pulsatilla chinensis* saponin B4 is not less than 90% determined by HPLC), or that obtained by chemical synthesis (with a content ≥90% determined by HPLC).

In this specification, unless otherwise indicated, said "water" is purified water that can be used for mucosal administration preparations, including but not limited to deionized water, re-distilled water, water for injection, etc.

In this specification, unless otherwise indicated, said "about" is used to express the approximate value of a specific value, which can also achieve equivalent results or effects. In this context, "about" may refer to values within 20%.

EXAMPLES

The present invention will be illustrated in the following by referring to specific examples. It will be understood by those skilled in the art that these examples are only used to illustrate the present invention and do not in any way limit the scope of the present invention.

The experimental methods in the following examples, unless otherwise specified, are conventional methods. The raw medicinal materials and reagents and so on used in the following examples are all commercially available, unless otherwise stated. Among them, the details of some reagents are as follows:

*Pulsatilla chinensis* saponin B4 (with a content of 98% determined by HPLC): Jiangxi Bencao Tiangong Technology Co., Ltd., batch No.: 20170301;

Carbomer 941 (CP-941): Beijing Guoren Yikang Technology Co., Ltd., batch No.: 20120325;

Carbomer 980 (cp-980): Anhui Newman Fine Chemical Co., Ltd;

Hydroxypropylmethylcellulose (HPMC): Anhui Shanhe Pharmaceutical Accessories Co., Ltd., batch No.: 120602:

Sodium carboxymethylcellulose (CMC-Na): Anhui Shanhe Pharmaceutical Accessories Co., Ltd., batch number: 130601;

Mixed fatty acid glyceride type 34, mixed fatty acid glyceride type 36 and mixed fatty acid glyceride type 38: Hubei Zhongliao Chemical Co., Ltd., batch No.: 160325;

Glycerin: Xilong Chemical Co., Ltd., batch No.: 120914.

Experimental Example 1 Study on Rectal Gel of *Pulsatilla chinensis* Saponin B4

The formulation of rectal gel of *Pulsatilla chinensis* saponin B4 was preliminarily determined to be consisted of:

*Pulsatilla chinensis* saponin B4 (hereinafter abbreviated as "B4"), matrix, glycerin (humectant), triethanolamine (pH controlling agent), deionized water.

The preparative method for rectal gel of *Pulsatilla chinensis* saponin B4 in this experimental example is as follows:

*Pulsatilla chinensis* saponin B4 is dissolved in water and filtrated, to obtain the aqueous solution of *Pulsatilla chinensis* saponin B4; to the resultant solution is slowly added the matrix under stirring, and the mixture is gently mixed; the mixture is further stirred, to which glycerin is added; triethanolamine is finally added to adjust pH to 6-7; stirring is continued until the swelling is uniform, and provided the rectal gel.

1. Screening of Matrix

The ingredients were provided according to the prescription composition shown in Table 1, and the gel was prepared according to the same method. CP-941, CP-980, HPMC and CMC-Na were investigated by using the appearance, viscosity, spreadability and stability of the gel as an index. The results are shown in Table 1.

TABLE 1

Effect of different matrix on gel

| Matrix | 0.5%[a] CP-941 | 0.5%[a] CP-980 | 0.5%[a] HPMC | 0.5%[a] CMC-Na |
|---|---|---|---|---|
| B4 | 1.2% | 1.2% | 1.2 | 1.2 |
| Glycerol | 10% | 10% | 10 | 10 |
| Triethanolamine | 0.5% | 0.5% | 0.5% | 0.5% |
| Deionized water | Added to 100% | Added to 100% | Added to 100% | Added to 100% |
| 55° C./6 h | no layering | no layering | no layering | no layering |
| −20° C./24 h | no layering | no layering | no layering | no layering |
| 3000 rounds/15 min | no layering | no layering | no layering | no layering |
| Viscosity | suitable | thicker | bad | bad |
| Spreadability | good | hard to spread | very watery | Very watery |
| Appearance | colorless transparent semisolid, indicating bright color | colorless transparent semi-solid, slightly rough surface | Colorless transparent fluid | Colorless transparent fluid |

[a]mass percentage, so do for others.

Table 1 shows that HPMC and CMC-Na can not form gels at this concentration, in that the viscosity is small, presenting the liquid state; while CP-941 and CP-980 have good formability, but the gel formed by CP-980 is thicker and not easy to spread, as well as the surface is slightly rough compared with CP-941. Therefore, the comprehensive order of rectal gel formed by different substrates is CP-941>CP-980>HMPC≈CMC-Na. Thus, in the present invention, CP-941 and CP-980 are preferably selected as matrix of rectal gel of *Pulsatilla chinensis* saponin B4, and most preferably, the matrix is CP-941.

2. Screening of the Amount of CP-941

Each ingredient is provided according to the formulation composition shown in Table 2, and the gel is prepared as the same method. Taking the appearance, viscosity, spreadability and stability of the gel as an index, the amount of CP-941 (0.25%, 0.5%, 1%) was investigated.

TABLE 2

Investigation on the amount of CP-941

| No. | 1 | 2 | 3 |
|---|---|---|---|
| B4 (%) | 1.2 | 1.2 | 1.2 |
| CP-941 (%) | 0.25 | 0.5 | 1.0 |
| glycerol (%) | 10 | 10 | 10 |
| triethanolamine (%) | 0.25 | 0.5 | 1.0 |
| deionized water(%) | added to 100% | added to 100% | added to 100% |
| 55° C./6 h | no layering | no layering | no layering |
| −20° C./24 h | no layering | no layering | no layering |
| 3000 rounds/15 min | no layering | no layering | no layering |
| viscosity | more watery | suitable | thicker |
| spreadability | easy to spread, but wet | good | not easy to spread |
| appearance | colorless transparent | colorless and transparent | colorless and translucent |

[a]mass percentage

Table 2 shows that when the usage amount of carbomer 941 was 0.25% or 1%, the gel viscosity is thinner or thicker, and spreadability is not good. When it was used at 0.5%, both viscosity and spreadability of the gel are superior to that obtained by 0.25% and 1%. Therefore, the comprehensive ranking for the gels obtained by different amount of carbomer 941 is: 0.5%>0.25%>10%, and the best amount is about 0.5%.

3. Screening of Amount of Glycerol

Each ingredient is provided according to the formulation composition shown in Table 3, and the gel is prepared as the same method. Taking the appearance, viscosity, spreadability, stability, and moisture retention of the gel as an index, the amount of glycerol was investigated. The results are shown in Tables 3 and 4.

TABLE 3

Investigation on the amount of glycerol

| No. | 1 | 2 | 3 |
|---|---|---|---|
| B4 (%) | 1.2 | 1.2 | 1.2 |
| CP-941 (%) | 0.25 | 0.5 | 1.0 |
| glycerol(%) | 5 | 10 | 15 |
| triethanolamine(%) | 0.5 | 0.5 | 0.5 |
| deionized water(%) | added to 100% | added to 100% | added to 100% |
| 55° C./6 h | no layering | no layering | no layering |
| −20° C./24 h | no layering | no layering | no layering |
| 3000 rounds/15 min | no layering | no layering | no layering |
| viscosity | suitable | suitable | suitable |
| spreadability | good | good | good |
| appearance | colorless, transparent | colorless, transparent | colorless, transparent |

$^a$: mass percentage

As shown in Table 3, the viscosity, spreadability, and stability for 3 batches of gels prepared are similar.

TABLE 4

Effect of the content of glycerol on the water loss rate of gel (n = 3, $\overline{X} \pm s$)

| Content of glycerol (%) | 0.5 h | 1.0 h | 2.0 h | 4.0 h | 6.0 h |
|---|---|---|---|---|---|
| 5 | 3.7 ± 0.8 | 4.4 ± 0.9 | 6.8 ± 1.0 | 10.5 ± 1.6 | 18.1 ± 2.1 |
| 10 | 4.2 ± 0.7 | 4.0 ± 0.5 | 6.1 ± 1.6 | 9.4 ± 0.9 | 15.2 ± 1.1 |
| 15 | 5.3 ± 1.4 | 4.5 ± 0.8 | 7.9 ± 0.5 | 13.2 ± 1.5 | 21.5 ± 1.2 |

But as shown in Table 4, taking the water loss rate as the index (the lower the water loss rate, the better the moisture retention), the ranking of the gel with different content of glycerol is: 10% glycerol>5% glycerol>15% glycerol. Therefore, in the rectal gel of *Pulsatilla chinensis* saponin B4 according to the present invention, the amount of humectant glycerol can be about 5%-15% (mass percent), preferably about 5%-10% (mass percentage), and most preferably about 10% (mass percentage).

4. Conclusion

Taking the appearance, viscosity, spreadability, stability, and moisture retention of the gel as an index, by screening, the best gel matrix was carbomer 941, which accounted for 0.25%-0.5% of the total mass of gel, preferably 0.4%-0.6%. The amount of glycerol was 5%-15%, preferably 5%-10%.

Based on this, the optimum formulation for rectal gel of *Pulsatilla chinensis* saponin B4 is:

*Pulsatilla chinensis* saponin B4, carbomer 941, glycerol, triethanolamine, and water, pH=6-7; wherein, based on the total mass of rectal gel of *Pulsatilla chinensis* saponin B4, the mass percentage of carbomer 941 is 0.25%-0.5%, the mass percentage of glycerol is 5%-15%, and the mass ratio of carbomer 941, triethanolamine, and glycerol is 1:1:15-1:1:25.

Further preferably, the formulation for rectal gel of *Pulsatilla chinensis* saponin B4 is:

*Pulsatilla chinensis* saponin B4, carbomer 941, glycerol, triethanolamine, and water, pH=6-7; wherein, based on the total mass of rectal gel of *Pulsatilla chinensis* saponin B4, the mass percentage of carbomer 941 is 0.4%-0.6%, the mass percentage of glycerol is 5%-12%, and the mass ratio of carbomer 941, triethanolamine, and glycerol is 1:1:20.

Example 1 A Rectal Gel of *Pulsatilla chinensis* Saponin B4

Formula:

| Pulsatilla chinensis saponin B4 | 1.2 g |
|---|---|
| carbomer941 | 0.4 g |
| glycerol | 8 g |
| triethanolamine | 0.4 g |
| deionized water | 72 mL |

Preparative Method:

Accurately weigh/measure each component according to the formula: *Pulsatilla chinensis* saponin B4 was dissolved in deionized water (under magnetic stirring) and filtrated, to obtain the aqueous solution of *Pulsatilla chinensis* saponin B4; to the resultant solution was slowly added carbomer 941 under stirring for 20 min until mixed well; then glycerin was added, and the mixture was stirred for additional 3 min; triethanolamine was finally added to adjust pH to 6-7, and the mixture was further stirred to obtain the hydrogel preparation of *Pulsatilla chinensis* saponin B4 (65 ml), in which the content of *Pulsatilla chinensis* saponin B4 was about 17.46 mg/mL.

Example 2 A Rectal Gel of *Pulsatilla chinensis* Saponin B4

Formula:

| Pulsatilla chinensis saponin B4 | 2.0 g |
|---|---|
| carbomer 941 | 0.25 g |
| glycerol | 5 g |
| triethanolamine | 0.25 g |
| deionized water | 91.5 mL |

Preparative Method:

The preparative method was the same as that in example 1, 80 mL of the hydrogel preparation of *Pulsatilla chinensis* saponin B4 was obtained, in which the content of *Pulsatilla chinensis* saponin B4 was about 23.92 mg/mL.

Example 3 A Rectal Gel of *Pulsatilla chinensis* Saponin B4

Formula:

| Pulsatilla chinensis saponin 94 | 0.75 g |
|---|---|
| carbomer941 | 0.4 g |
| glycerol | 8 g |
| triethanolamine | 0.4 g |
| deionized water | 90.45 mL |

Preparative Method:

The preparative method was the same as that in example 1, 79 mL of the hydrogel preparation of *Pulsatilla chinensis* saponin B4 was obtained, in which the content of *Pulsatilla chinensis* saponin B4 was about 8.73 mg/mL.

Example 4 A Rectal Gel of *Pulsatilla chinensis* Saponin B4

Formula:

| | |
|---|---|
| Pulsatilla chinensis saponin B4 | 2.5 g |
| Carbomer 941 | 0.25 g |
| glycerol | 5 g |
| triethanolamine | 0.25 g |
| deionized water | 91.5 mL |

Preparative Method:

The preparative method was the same as that in example 1, 80 mL of the hydrogel preparation of *Pulsatilla chinensis* saponin B4 was obtained, in which the content of *Pulsatilla chinensis* saponin B4 was about 29.75 mg/mL.

Example 5 A Rectal Gel of *Pulsatilla chinensis* Saponin B4

Formula:

| | |
|---|---|
| Pulsatilla chinensis saponin B4 | 1.8 g |
| carbomer941 | 0.6 g |
| glycerol | 12 |
| triethanolamine | 0.6 g |
| deionized water | 85 mL |

Preparative Method:

The preparative method was the same as that in example 1, 74 mL of the hydrogel preparation of *Pulsatilla chinensis* saponin B4 was obtained, in which the content of *Pulsatilla chinensis* saponin B4 was about 22.42 mg/mL.

Experimental example 2 Study on suppository of *Pulsatilla chinensis* saponin B4 *Pulsatilla chinensis* saponin B4 has good water solubility, and in order to make the drug be absorbed better in the cavity and prevent the deformation of the suppository or the growth of microorganisms such as mycetes caused by the moisture absorption of the drug, the oil matrix was used in the suppository of the present invention. In the oil matrix, the mixed fatty acid glyceride was non-toxic, non-irritant, stable in nature, appropriate in price, reliable in supply, and has different melting points so that the matrix can be chosen according to the requirements of the drug.

Therefore, the mixed fatty acid glyceride was used as the matrix of the suppository of the present invention. By this experimental example, the model of mixed fatty acid glycerides and the preparation technology were investigated and screened.

1. Screening of Matrix

In this experiment, the appearance, melting time and melting point of the product were used as the indexes to investigate three different types of matrix, i.e. types 34, 36 and 38 of mixed fatty acid glycerides.

4 g each of above three types of matrices was weighed, put into an evaporating dish respectively, and heated in a 55° C. water bath to make them melt completely, to which was added 450 mg raw powders of *Pulsatilla chinensis* saponin B4 under stirring, respectively. Then, the mixture was injected into the mould (with a temperature of about 20° C.) which has been uniformly coated with liquid paraffin, cooled for 30 min, and the overflow part was scraped off, then the rectal suppository is provided.

When judging the appearance, the resultant suppository was put under the white glossy paper, and the appearance of suppository was observed under the daily light. The observation indexes included the uniformity of color, the smoothness of suppository and the comfort of touching with hands. When measuring the melting time, three suppositories of each type were respectively placed on the lower layers of three circular metal plates after kept for 30 min at room temperature, then the plate was installed into their respective stainless steel grids and turned over regularly. Meanwhile, the temperature was controlled at 37° C. to measure the melting time. At the same time, the melting point was determined according to the second of 0612 melting point determination methods in the fourth part of Pharmacopoeia 2015. The results are shown in Table 5.

TABLE 5

Determination and screening results of different types of matrices

| Evaluation index | Type 34 | Type 36 | Type 38 |
|---|---|---|---|
| appearance | uniform and smooth | uniform and smooth | A few depressed points |
| Melting time (min) | 24 | 20 | 18 |
| Melting point ° C. | 35.5° C. | 36.8° C. | 37.2° C. |

According to the results shown in Table 5, types 36 and 34 of mixed fatty acid glycerol esters have obvious advantages in the appearance of the products, and the melting point of the suppository prepared by type 36 matrix is about 37° C., meeting the general requirements.

Therefore, the suppository matrix of *Pulsatilla chinensis* saponin B4 is preferably selected from one or both of mixed fatty acid glycerides 34 or 36, and more preferably from mixed fatty acid glyceride 36.

2. Selection of Heating Temperature of Matrix

The temperature should not be too high when heating to melt semi-synthetic fatty acid glycerides. When two-thirds or three-quarters melted, stop heating and let the matrix melt by itself, so that the temperature after complete melting is about 50° C. Before injection into the mould, the temperature should be controlled at about 40° C. If the temperature is too high, the cooling time will be prolonged, during which the powder may precipitate and cause uneven content. Therefore, the effect of heating and melting temperature of matrix on the formation of suppository was investigated in this experiment.

Three parts of matrices of mixed fatty acid glycerol esters (type 36) were taken out, each being 4 g, and when about three-quarters of matrices melted at 55° C., 60° C. and 65° C., respectively, heating was removed, while stirring was still continued. After the temperature was cooled to 50° C. and the matrices almost completely melted, 450 mg raw powders of *Pulsatilla chinensis* saponin B4 were added into the melted matrix, respectively. After thoroughly stirring, the mixture was injected into the mould which has already been evenly coated with liquid paraffin (the temperature of mould being about 20° C.). After cooling for 30 min the overflow part was scraped off to obtain the suppository product. The appearance was observed to select the best heating temperature of substrate. The results are shown in Table 6.

TABLE 6

| Investigation on heating temperature of matrix | | | |
|---|---|---|---|
| Heating temperature | 55° C. | 60° C. | 65° C. |
| appearance | uniform and smooth | uniform and smooth | uniform and smooth |

According to the results in Table 6, when heated at three test temperatures, all of the matrices melted, and then were cooled to about 50° C. for molding. The appearance of resultant suppository was smooth and uniform, without significant difference. Therefore, type 36 of the mixed fatty acid glyceride can achieve the same effect when heated and melted at 55-65° C. In order to shorten the time when the substrate temperature was reduced to 50° C., a heating temperature of about 55° C. can be selected.

3. Conclusion

For the rectal suppository of *Pulsatilla chinensis* saponin B4 according to the present invention, the matrix is oily, and preferably selected from one or both of types 34 and 36 of the mixed fatty acid glycerides, and more preferably from type 36 of the mixed fatty acid glycerides. The preparative process and conditions are as follows:

Said matrices are heated at the temperature of 55-65° C. till ⅔-¾ of them are melting, then stopped heating, and stirred till the matrices are completely melted. Upon the matrix temperature is reduced to 50±2° C., *Pulsatilla chinensis* saponin B4 is added. The mixture is stirred to disperse evenly, and injected into the suppository mould which has been evenly coated with liquid paraffin (the mould temperature being about 20° C.). After cooling for 30 minutes, the overflow part is scraped off, and then the rectal suppository is provided;

More preferably, said preparative process and conditions are as follows:

Said matrices are heated at the temperature of about 55° C. till ⅔-¾ of them are melting, then stopped heating, and stirred till the matrices are completely melted. Upon the matrix temperature is reduced to 50±2° C., *Pulsatilla chinensis* saponin B4 is added. The mixture is stirred to disperse evenly, and injected into the suppository mould which has been evenly coated with liquid paraffin (the mould temperature being about 20° C.). After cooling for 30 minutes, the overflow part is scraped off, and then the rectal suppository is provided;

For above rectal suppository of *Pulsatilla chinensis* saponin B4, the content of B4 in each suppository may be 50-200 mg.

Example 6 A Rectal Suppository of *Pulsatilla chinensis* Saponin B4

Formula:

| | |
|---|---|
| Pulsatilla chinensis saponin B4 | 4500 mg, |
| Mixed fatty acid glycerides (type 36) | 40 g. |

Preparative Method:

Each ingredient was weighed according to the formula, and the mixed fatty acid glycerides (type 36) was placed in an evaporating dish and heated to 55° C., till about ¾ of them were melting, then stopped heating, and continued to stirred. Upon the temperature was reduced to about 50° C., *Pulsatilla chinensis* saponin B4 was added to the completely melted matrices. The mixture was stirred to disperse evenly, and injected into the suppository mould which has been evenly coated with liquid paraffin (the mould temperature being about 20° C.). After cooling for 30 minutes, the overflow part is scraped off, and then the rectal suppository is provided.

A total of 40 suppositories were prepared, and each weighed about 1 g. The surface was smooth and uniform, and each suppository contained *Pulsatilla chinensis* saponin B4 at 112.5 mg/suppository.

Example 7 A Rectal Suppository of *Pulsatilla chinensis* Saponin B4

Formula:

| | |
|---|---|
| Pulsatilla chinensis saponin B4 | 5400 mg, |
| Mixed fatty acid glycerides (type 36) | 40 g. |

Preparative Method:

Each ingredient was weighed according to the formula, and the mixed fatty acid glycerides (type 36) was placed in an evaporating dish and heated to 60° C., till about ⅔ of them were melting, then stopped heating, and continued to stirred. Upon the temperature was reduced to about 50° C., *Pulsatilla chinensis* saponin B4 was added to the completely melted matrices. The mixture was stirred to disperse evenly, and injected into the suppository mould which has been evenly coated with liquid paraffin (the mould temperature being about 20° C.). After cooling for 30 minutes, the overflow part is scraped off, and then the rectal suppository is provided.

A total of 40 suppositories were prepared, and each weighed about 1 g. The surface was smooth and uniform, and each suppository contained *Pulsatilla chinensis* saponin B4 at 135 mg/suppository.

Example 8 A Rectal Suppository of *Pulsatilla chinensis* Saponin B4

Formula:

| | |
|---|---|
| Pulsatilla chinensis saponin 94 | 4500 mg, |
| Mixed fatty acid glycerides (type 34) | 40 g. |

Preparative Method:

Each ingredient was weighed according to the formula, and the mixed fatty acid glycerides (type 34) was placed in an evaporating dish and heated to 65° C., till about ⅔ of them were melting, then stopped heating, and continued to stirred. Upon the temperature was reduced to about 50° C., *Pulsatilla chinensis* saponin B4 was added to the completely melted matrices. The mixture was stirred to disperse evenly, and injected into the suppository mould which has been evenly coated with liquid paraffin (the mould temperature being about 20° C.). After cooling for 30 minutes, the overflow part is scraped off, and then the rectal suppository is provided.

A total of 40 suppositories were prepared, and each weighed about 1 mg. The surface was smooth and uniform, and each suppository contained *Pulsatilla chinensis* saponin B4 at 112.5 mg/suppository.

Experimental Example 3 Pharmacodynamic Study on Rectal Mucosa Administration Preparation of *Pulsatilla chinensis* Saponin B4 According to the Present Invention 1. Effects of Different B4 Preparations on Gentamicin-Induced Acute Kidney Injury in Rats Gentamicin-induced acute renal failure (ARF) model mainly caused renal tubular cell injury by affecting lipid metabolism of renal tubular epithelial cell membrane and inhibiting energy metabolism of mitochondria. Acute renal failure induced by gentamicin was mainly manifested in the increase of creatinine and urea nitrogen, but the mechanism of gentamicin induced nephrotoxicity was still unclear. In this experiment, two kinds of rectal mucosa administration preparations of *Pulsatilla chinensis* saponin B4 according to the present invention were infused by anus to observe the preventive and therapeutic effects of tested drugs on gentamicin-induced ARF in rats, and compared with oral (gavage) administration of *Pulsatilla chinensis* saponin B4.

1.1 Experimental Animals and Experimental Materials 1.1.1 Animal: SD rats. SPF grade, 180-200 g, male, Hunan SJA Laboratory Animal Co., Ltd., license No.: SCXK (Xiang) 2016-0002.

1.1.2 Reagent: gentamicin sulfate injection, Henan Runhong Pharmaceutical Co., Ltd., product batch number: 1610202, 2 ml/80 mg each.

1.1.3 Drug: gel of *Pulsatilla chinensis* saponin B4 prepared in example 1 (abbreviated as "B4 gel"); suppository of *Pulsatilla chinensis* saponin B4 prepared in example 6 (abbreviated as "B4 suppository"); *Pulsatilla chinensis* saponin B4 (abbreviated as "B4 raw powder"); Dexamethasone, 0.75 g/tablet. Anhui Golden Sun Biochemical Pharmaceutical Co., Ltd., batch No.: 16032521.

Dexamethasone solution: 4 tablets of dexamethasone were ground and dissolved in 100 ml double distilled water, and then diluted to 0.03 mg/ml.

B4 raw powder solution: 2000 mg of B4 raw powder was weighed, ground, and dissolved in 100 ml double distilled water to obtain 20 mg/ml solution.

1.1.4 Apparatus: table-type low-speed centrifuge; automatic biochemical analyzer; enzyme-linked immunosorbent assay (ELISA)

1.2 Experimental Method 1.2.1 Preparation before modeling

All animals were numbered and weighed, then the data were recorded.

1.2.2 Modeling method

Rats in experimental groups were intraperitoneally injected with gentamicin sulfate solution at the dose of 140 mg/kg, while the rats in the blank group were intraperitoneally injected with equal volume of normal saline, and the administration was continued for 7 days to make a model.

1.2.3 Grouping and Administration

The animals were randomly divided into blank group; model group; positive drug group (dexamethasone group); B4 gel high, medium, and low dose groups; B4 suppository high, medium, and low dose groups; B4 powder group; 10 animals for each group. Animals in B4 gel groups received the gel by rectum at 0.3 ml/100 g body weight; animals in B4 suppository groups received the suppository by rectum; B4 raw powder group and positive group were given corresponding drugs by gavage according to 10 ml/kg body weight. The model group and the blank group were given the same volume of double distilled water by gavage. The drug was continuously administered for 7 days from the second day of modeling.

1.2.4 Index detection

Urine proteins were detected by Coomassie brilliant blue method. After isoflurane anesthesia, blood samples were taken from eyeballs of rats. Serum was separated. Total protein (TP), urea nitrogen (BUN), and creatinine (CRE) were detected by automatic biochemical analysis.

1.3 Experimental Results 1.3.1 Effects of different preparations on serum indexes of gentamicin-induced acute kidney injury in rats Results are shown in Table 7.

TABLE 7

Effects of different B4 preparations on serum indexes of gentamicin-induced acute kidney injury in rats.
(SD ± Mean)

| Groups | Doses mg/kg | TP (g/L) | BUN (mg/dl) | CREA (μmol/L) |
|---|---|---|---|---|
| Blank group | / | 59.7 ± 1.6 | 10.4 ± 2.2 | 22.8 ± 2.1 |
| Model group | / | 51.2 ± 3.8## | 156.9 ± 38.4## | 291.7 ± 100.9## |
| Dexamethasone group | 0.3 | 65.7 ± 5.8** | 79.3 ± 33.6** | 83.2 ± 31.9** |
| B4 gel high dose group | 200 | 58.0 ± 3.0ΔΔ | 52.3 ± 22.8ΔΔ | 120.7 ± 53.0**ΔΔ |
| B4 gel medium dose group | 100 | 55.9 ± 3.3* | 84.5 ± 37.7** | 126.8 ± 45.5** |
| B4 gel low dose group | 50 | 54.8 ± 4.1* | 110.9 ± 33.7* | 244.8 ± 86.0 |
| B4 suppository high dose group | 200 | 57.0 ± 1.8ΔΔ | 62.9 ± 37.1ΔΔ | 139.2 ± 50.1**Δ |
| B4 suppository medium dose group | 100 | 55.8 ± 2.3* | 89.3 ± 21.4** | 149.5 ± 46.3** |
| B4 suppository low dose group | 50 | 55.5 ± 3.1* | 118.7 ± 42.8* | 262.6 ± 105.0 |
| B4 raw powder group | 200 | 53.2 ± 4.3 | 126.4 ± 37.6 | 268.7 ± 56.2 |

Note:
compared with the blank group, #$p < 0.05$, ##$p < 0.01$; compared with the model group, *$p < 0.05$, **$p < 0.01$; Compared with B4 raw powder group, Δ$p < 0.05$, ΔΔ$p < 0.01$.

Data in Table 7 show:

(1) Seven days after modeling, compared with the blank group, in model group BUN and CREA in serum increased significantly (P<0.01), while TP decreased significantly (P<0.01) indicating that the model was successfully established.

(2) Compared with the model group. B4 gel groups (including high, medium, and low doses) and B4 suppository groups (including high, medium, and low doses) showed significant or extremely significant increase in TP level (P<0.05 or P<0.01), while B4 raw powder group didn't show significant difference. In addition, compared with B4 raw powder group, in the high dose groups of both B4 gel and B4 suppository the increased level of TP had significant difference (P<0.01); For medium dose groups of B4 gel and B4 suppository, although there was no significant difference in comparison with B4 raw powder group, but the levels of TP in the two rectum administration groups were higher than that in the oral administration group.

(3) Compared with the model group, B4 gel groups (including high, medium, and low doses) and B4 suppository groups (including high, medium, and low doses) showed significant or extremely significant decrease in BUN level (P<0.01 or P<0.05), as well as B4 raw powder group also showed significant decrease in BUN level (P<0.05); However, the level of BUN in each dose group of B4 rectal administration was lower than that of the oral administration group, and BUN level in high dose groups of B4 gel and B4 suppository decreased more and showed significant difference (P<0.01) compared with the B4 raw powder group.

(4) Compared with the model group, high and medium dose groups for both B4 gel and B4 suppository showed extremely significant decrease in CREA level (P<0.01), and B4 raw powder group also showed significant decrease in CREA level (P<0.05); However, the level of CREA in each dose group of B4 rectal administration was all lower than that of the oral administration group, and CREA level in high dose groups of B4 gel and B4 suppository decreased more and showed significant or extremely significant difference (P<0.05 or P<0.01) compared with the B4 raw powder group.

Conclusion:

Based on above results, under the same dosage, B4 gel and B4 suppository of the present invention had better protective effect on renal function than the raw powder administered orally. More importantly, the dosage of B4 gel and B4 suppository is only half of that of raw powder, but both of them reversed gentamicin-induced acute kidney injury in rats, and the effects were equivalent to that of oral raw powder, or even slightly better.

1.3.2 Effects of different b4 preparations on urinary proteins in gentamicin-induced acute kidney injury of rats Results are shown in Table 8.

TABLE 8

Effects of different B4 preparations on urinary proteins in gentamicin-induced acute kidney injury of rats

| Group | Dose (mg/kg) | Urinary Protein (mg/ml) | | |
|---|---|---|---|---|
| | | 5th day of administration | 6th day of administration | 7th day of administration |
| Blank group | / | 3.46 ± 0.66 | 2.51 ± 0.69 | 2.93 ± 0.54 |
| Model group | / | 5.46 ± 0.58## | 5.51 ± 0.67## | 5.98 ± 1.31## |
| Dexamethasone group | 0.3 | 5.15 ± 0.89 | 5.52 ± 1.36 | 5.63 ± 0.58 |
| B4 gel high dose group | 200 | 4.13 ± 1.08*△ | 4.26 ± 1.16**△ | 4.24 ± 1.54**△ |
| B4 gel medium dose group | 100 | 4.57 ± 1.24* | 4.61 ± 1.41* | 4.73 ± 0.84* |
| B4 gel low dose group | 50 | 4.84 ± 1.23 | 5.10 ± 1.12 | 5.24 ± 0.44 |
| B4 suppository high dose group | 200 | 4.19 ± 1.38*△ | 4.27 ± 0.99*△ | 4.60 ± 0.77**△ |
| B4 suppository medium dose group | 100 | 4.58 ± 1.11* | 4.66 ± 1.26* | 4.81 ± 1.19* |
| B4 suppository low dose group | 50 | 4.99 ± 1.16 | 5.07 ± 1.22 | 5.23 ± 1.20 |
| B4 raw powder group | 200 | 4.86 ± 1.22 | 5.18 ± 1.15 | 5.38 ± 0.92 |

Note:
compared with the blank group, #P < 0.05, ##P < 0.01; compared with the model group, *P < 0.05, **P < 0.01; Compared with B4 raw powder group, △P < 0.05, △△P < 0.01.

Data in Table 8 show:

(1) On the 5th, 6th and 7th days of administration, compared with the blank group, the content of urinary protein in the model group was significantly increased (P<0.01) indicating that the model was successfully established.

(2) Compared with model group, B4 gel high and medium dose groups, as well as B4 suppository high and medium dose groups had significantly lower urinary protein contents on 5th, 6th, 7th days of administration (P<0.01 or P<0.05), and all of them showed significant difference compared with B4 raw powder group (P<0.05).

(3) The urine protein levels of B4 gel low dose group, B4 suppository low dose group and B4 raw powder group showed a decreased trend on fifth, sixth, seventh days of administration, but there was no statistical significance compared with model group.

Conclusion:

Based on above results, B4 gel and B4 suppository could significantly reduce the level of urinary protein in rats with acute kidney injury induced by gentamycin, while oral administration of B4 could not reverse the increase of urinary protein. Therefore, the effect of B4 rectal administration preparation of the present invention is significantly better than that of B4 oral preparation.

1.4 Conclusion

According to above results, B4 gel and B4 suppository could significantly improve the renal function (creatinine and urea nitrogen) in rats with acute kidney injury induced by gentamycin, reduce the excretion of urinary protein, increase the total protein content in the serum (total protein), and have a better protective effect on acute kidney injury rats. B4 raw powder (oral administration) had a tendency to improve the renal function of rats with acute kidney injury. In comparison with these dosage forms (different routes of administration), it was found that the therapeutic effects of B4 gel and B4 suppository of the present invention administrated by rectum were much better than that of oral B4 raw powder, and the dosage was lower. That indicated the rectal administration preparation of *Pulsatilla chinensis* saponin B4 according to the present invention could improve the efficacy with reduced dosage, thus increasing the safety window of clinical medication.

2. Effects of Different B4 Preparations on Cisplatin-Induced Acute Kidney Injury in Mice After intraperitoneal injection of cisplatin, cisplatin was toxic to different parts of the kidney. It could cause changes in the function and morphology of glomerulus and renal tubules. Cisplatin could cause renal vasoconstriction, reduce renal blood flow and glomerular filtration rate, and thus cause proteinuria, renal function damage and other symptoms. In this study, B4 was administered by different routes (rectum and oral) to observe the preventive and therapeutic effects of B4 on cisplatin-induced ARF in mice.

2.1 Experimental Materials 2.1.1 Animal: ICR mice, 16-18 g, male, Hunan SJA Laboratory Animal Co., Ltd., license No.: SCXK (Xiang) 2016-0002.

2.1.2 Reagent: cisplatin, the original solution 5 mg/kg. Prior to use, cisplatin was added with suitable amount of normal saline to prepare 1.5 mg/ml solution for use.

2.1.3 Drug: gel of *Pulsatilla chinensis* saponin B4 prepared in example 1 (abbreviated as "B4 gel"); suppository of *Pulsatilla chinensis* saponin B4 prepared in example 6 (abbreviated as "B4 suppository"); *Pulsatilla chinensis* saponin B4 (abbreviated as "B4 raw powder"); Dexamethasone, 0.75 g/tablet, Anhui Golden Sun Biochemical Pharmaceutical Co., Ltd., batch No.: 16032521.

Dexamethasone solution: 4 tablets of dexamethasone were ground and dissolved in 100 ml double distilled water, and then diluted to 0.03 mg/ml.

B4 raw powder solution: 1000 mg of B4 raw powder was weighed, ground, and dissolved in 100 ml double distilled water to obtain 10 mg/ml solution.

2.1.4 Apparatus: table-type low-speed centrifuge; automatic biochemical analyzer 2.2 Experimental Method 2.2.1 Preparation before modeling All animals were numbered and weighed, then the data were recorded.

2.2.2 Modeling method

The model was established by cisplatin at a dosage of 15 ml/kg. The normal group was intraperitoneally injected with normal saline, and the other groups were intraperitoneally injected with cisplatin injection.

2.2.3 Grouping and administration

The animals were randomly divided into blank group; model group; positive drug group (dexamethasone group); B4 gel high, medium, and low dose groups; B4 suppository high, medium, and low dose groups; B4 raw powder group; 10 animals for each group. Animals in B4 gel groups received the gel by rectum at 0.3 ml/100 g body weight; animals in B4 suppository groups received the suppository by rectum; B4 raw powder group and positive group were given corresponding drugs by gavage according to 20 m/kg body weight. The model group and the blank group were given the same volume of double distilled water by gavage. The drug was continuously administered for 4 days from the day of modeling. Animals were fasted for 16-18 hours before administration on day 4.

2.2.4 Index detection

One hour after the last administration, urine was collected to measure urine proteins. Blood samples were taken from eyeballs to separate serum. Total protein (TP), urea nitrogen (BUN) and creatinine (Cre) were detected by automatic biochemical analysis.

2.3 Experimental Results: See Table 9.

TABLE 9

Effects of different B4 preparations on cisplatin-induced acute kidney injury in mice (SD ± Mean).

| Groups | dose mg/kg | TP (g/L) | BUN (mg/dl) | CREA (μmol/L) | Urinary Protein mg/ml |
|---|---|---|---|---|---|
| Blank group | / | 51.61 ± 2.31 | 25.14 ± 4.34 | 25.56 ± 4.00 | 0.89 ± 0.11 |
| Model group | / | 45.26 ± 2.19## | 61.95 ± 11.03## | 41.69 ± 3.66## | 1.76 ± 0.27## |
| Dexamethasone group | 0.6 | 52.90 ± 2.50** | 42.97 ± 17.45** | 30.10 ± 3.93** | 1.00 ± 0.24** |
| B4 gel high dose group | 400 | 49.79 ± 2.01Δ | 43.58 ± 16.95 | 31.88 ± 8.13 | 1.19 ± 0.19 |
| B4 gel medium dose group | 200 | 48.87 ± 2.36* | 49.79 ± 17.68* | 34.40 ± 7.07* | 1.35 ± 0.16** |
| B4 gel low dose group | 100 | 46.58 ± 2.25 | 54.40 ± 14.30 | 38.10 ± 375 | 1.53 ± 0.39 |
| B4 suppository high dose group | 400 | 49.43 ± 2.50**Δ | 44.26 ± 15.76* | 29.27 ± 5.66** | 1.18 ± 0.20** |
| B4 suppository medium dose group | 200 | 48.36 ± 2.10* | 50.89 ± 17.87* | 35.00 ± 4.24* | 1.21 ± 0.41* |
| B4 suppository low dose group | 100 | 46.25 ± 1.83 | 54.84 ± 25.27 | 39.70 ± 4.52 | 1.48 ± 0.41 |
| B4 raw powder group | 400 | 46.12 ± 2.27 | 55.86 ± 13.91 | 38.11 ± 9.56 | 1.55 ± 0.45 |

Note:
compared with the blank group, #P < 0.05, ##P < 0.01; compared with the model group, *P < 0.05, **P < 0.01; Compared with B4 raw powder group, ΔP < 0.05.

Data in Table 9 show:

(1) Compared with the blank group, the levels of BUN, CREA and urinary protein in serum of the model group were significantly increased (P<0.01), while the content of total serum protein (TP) was significantly decreased (P<0.01), indicating the model was successfully established.

(2) Compared with model group, B4 gel high and medium dose groups, as well as B4 suppository high and medium dose groups could significantly or extremely significantly increase the content of serum TP in mice with acute kidney injury (P<0.01 or P<0.05). The content of TP in low dose groups of B4 gel and B4 suppository as well as B4 raw powder group showed a weak trend of increasing. Compared with that of B4 raw powder group, the content of TP in high-dose groups of B4 gel and B4 suppository showed significant difference (P<0.05).

(3) Compared with the model group, high and medium dose groups for both B4 gel and B4 suppository could significantly or extremely significantly reduce the levels of BUN and CREA in serum of mice with acute kidney injury (P<0.01 or P<0.05); the levels of BUN and CREA in serum of low dose groups of B4 gel and B4 suppository as well as B4 raw powder group were somehow reduced, but there was no significant difference.

(4) Compared with the model group, high and medium dose groups for both B4 gel and B4 suppository could significantly or extremely significantly reduce the urinary protein level of mice with acute kidney injury (P<0.01 or P<0.05); the levels of urinary protein in low dose groups of B4 gel and B4 suppository as well as B4 raw powder group were somehow reduced, but there was no significant difference.

2.4 Conclusion

According to above results, B4 gel and B4 suppository could significantly improve the renal function in mice with acute kidney injury induced by cisplatin: lowering the levels of serum creatinine and urea nitrogen, reducing the excretion of urinary protein, and increasing the total protein content in serum, and having a better protective effect on mice with acute kidney injury. B4 raw powder (oral administration) had a tendency to decrease the content of BUN, CREA and urinary protein in serum, and also showed a trend of increasing serum total protein, but there was no significant difference compared with the model group. In comparison with different routes of administration, it was found that the therapeutic effects of B4 gel and B4 suppository of the present invention administrated by rectum were much better than that of oral B4 raw powder, and the effective dose was lower. That indicated the rectal administration preparation of *Pulsatilla chinensis* saponin B4 according to the present invention could effectively reduce the dose thereof, thus increasing the safety window.

In summary, the rectal mucosal administration preparation of *Pulsatilla chinensis* saponin B4 provided in the present invention has better effect on reversing and/or improving acute kidney injury caused by gentamicin and cisplatin than oral administration preparation, and has low effective dose and better safety, so it has obvious advantages.

The invention claimed is:

1. A rectal mucosal administration preparation, comprising 1%-20% of *Pulsatilla chinensis* saponin B4, 0.25%-0.5% of a carbomer, 5%-10% of a humectant, and 0.25%-5% of a pH controlling agent.

2. The rectal mucosal administration preparation according to claim 1, further comprising a substance selected from hydroxypropylmethylcellulose, a sodium carboxymethylcellulose, and mixtures thereof.

3. The rectal mucosal administration preparation according to claim 1 is a rectal gel, wherein,
   the humectant is selected from glycerol, propylene glycol, and mixtures thereof, and
   the pH controlling agent is selected from triethanolamine, sodium hydroxide, ethylenediamine, laurylamine, sodium bicarbonate, and mixtures thereof.

4. The rectal gel according to claim 3, having a pH value of 6-7, and comprises 0.25%-0.5% of carbomer 941, 5%-10% of glycerol, 0.25%-5% of triethanolamine, and for a balance of water.

5. The method for preparation of rectal gel of *Pulsatilla chinensis* saponin B4 according to claim 4, comprising:
   dissolving *Pulsatilla chinensis* saponin B4 is dissolved in water and filtered to obtain an aqueous solution; adding carbomer and humectant into the aqueous solution under stirring to form a uniform dispersion; adding said pH controlling agent to the uniform dispersion is added pH to 6-7 to obtain the rectal gel.

6. A method for treating acute renal injury, comprising administering the rectal mucosal administration preparation of claim 1 to a patient in need thereof.

7. The method of claim 6, wherein the rectal mucosal administration preparation is a rectal gel or a rectal suppository.

8. The method of claim 6, wherein the rectal mucosal administration preparation further comprises a pharmaceutically acceptable substance selected from hydroxypropylmethylcelluloses, sodium carboxymethylcelluloses, and mixtures thereof.

9. The method of claim 6, wherein the carbomer chosen from carbomer 941, carbomer 980, or a mixture thereof.

10. The method of claim 9, wherein the carbomer is carbomer 941.

\* \* \* \* \*